(12) United States Patent
Knorr (10) Patent No.: US 9,561,522 B2
(45) Date of Patent: *Feb. 7, 2017

(54) ULTRASONIC TRANSMITTING AND RECEIVING DEVICE FOR THICKNESS AND/OR GRAMMAGE MEASUREMENT

(71) Applicant: Helmut Knorr, Utting am Ammersee (DE)

(72) Inventor: Helmut Knorr, Utting am Ammersee (DE)

(*) Notice: Subject to any disclaimer, the term of this patent is extended or adjusted under 35 U.S.C. 154(b) by 226 days.

This patent is subject to a terminal disclaimer.

(21) Appl. No.: 14/477,652

(22) Filed: Sep. 4, 2014

(65) Prior Publication Data

US 2014/0377450 A1    Dec. 25, 2014

Related U.S. Application Data

(63) Continuation-in-part of application No. 13/431,171, filed on Mar. 27, 2012, now Pat. No. 8,904,874.

(30) Foreign Application Priority Data

Mar. 28, 2011 (DE) .................. 10 2011 015 334

(51) Int. Cl.
*G01N 29/11* (2006.01)
*G01N 29/04* (2006.01)
(Continued)

(52) U.S. Cl.
CPC .............. *B05C 5/00* (2013.01); *G01B 17/02* (2013.01); *G01B 17/025* (2013.01); *G01N 29/11* (2013.01);
(Continued)

(58) Field of Classification Search
CPC ......... G01B 17/02; G01B 21/08; B29C 47/92; B29C 47/0009; B29C 2947/92942; B29C 2947/92447; B29C 2947/92152; B29C 2947/92647; G01N 33/346; G01N 29/11; G01N 29/04
(Continued)

(56) References Cited

U.S. PATENT DOCUMENTS 4,113,358 A * 9/1978 Nakagawa ............ G02B 13/06
359/753
4,117,732 A * 10/1978 Brazhnikov ............ G01B 17/02
73/599

(Continued)

*Primary Examiner* — Helen Kwok
(74) *Attorney, Agent, or Firm* — Royse Law Firm, PC (57) ABSTRACT

An ultrasonic transmitting and receiving device is provided for measuring the transmission and/or reflection of ultrasonic waves on a thin material sheet, or a coating applied thereto. The device may include a plurality of ultrasonic transmitters, a plurality of ultrasonic receivers, wherein the number of the ultrasonic transmitters corresponds to the number of the ultrasonic receivers, and one receiver electronics respectively for each of the ultrasonic receivers or a group receiver electronics respectively for a predetermined number of ultrasonic receivers. A method is provided for ultrasonic absorption and/or transmission measurement, in which signals are emitted by multiple ultrasonic transmitters at the same time or nearly at the same time which are received by ultrasonic receivers and in which the received signals are evaluated in parallel.

23 Claims, 5 Drawing Sheets

(51) Int. Cl.
  *B05C 5/00* (2006.01)
  *G01B 17/02* (2006.01)
  *B29C 47/00* (2006.01)
  *B29C 47/92* (2006.01)
  *G01N 33/34* (2006.01)

(52) U.S. Cl.
  CPC ............ *B29C 47/0009* (2013.01); *B29C 47/92* (2013.01); *B29C 2947/92152* (2013.01); *B29C 2947/92447* (2013.01); *B29C 2947/92647* (2013.01); *B29C 2947/92942* (2013.01); *G01N 33/346* (2013.01); *G01N 2291/0237* (2013.01); *G01N 2291/0256* (2013.01); *G01N 2291/044* (2013.01); *G01N 2291/106* (2013.01)

(58) Field of Classification Search
  USPC ........ 73/632, 1.82, 159, 579, 597, 589, 602, 73/627, 628, 630
  See application file for complete search history.

(56) References Cited

U.S. PATENT DOCUMENTS

| | | | | |
|---|---|---|---|---|
| 4,446,735 A * | 5/1984 | Weilacher | ............. | G01B 17/02 73/159 |
| 4,545,251 A * | 10/1985 | Uchida | ............. | G01N 29/0609 73/1.82 |
| 4,669,312 A * | 6/1987 | Maurer | ............. | G01N 29/0618 73/599 |
| 4,676,647 A * | 6/1987 | Kikkawa | ............. | G01B 11/0625 356/328 |
| 4,730,473 A * | 3/1988 | Rottlander | ............. | B21D 39/10 72/12.7 |
| 4,810,894 A * | 3/1989 | Nagao | ............. | G01B 11/0616 250/559.12 |
| 5,077,478 A * | 12/1991 | Walford | ............. | G01N 23/203 250/358.1 |
| 5,138,178 A * | 8/1992 | Wong | ............. | B41J 11/20 177/1 |
| 5,327,770 A * | 7/1994 | Hindle | ............. | G01N 21/86 73/1.88 |
| 5,398,538 A * | 3/1995 | Williams | ............. | G01N 29/07 73/1.37 |
| 5,489,402 A * | 2/1996 | Knoblauch | ............. | B29C 47/92 264/171.11 |
| 5,621,173 A * | 4/1997 | Knorr | ............. | G01B 17/02 73/159 |
| 5,922,960 A * | 7/1999 | Toda | ............. | G01B 17/02 73/1.86 |
| 6,067,509 A * | 5/2000 | Gaiski | ............. | G01B 17/025 324/230 |
| 7,191,655 B2 * | 3/2007 | Matsuzawa | ............. | G01N 29/11 73/159 |
| 7,748,274 B2 * | 7/2010 | Pellaton | ............. | G01N 29/11 73/587 |
| 8,448,517 B2 * | 5/2013 | Itsumi | ............. | B65H 7/02 73/159 |
| 8,904,874 B2 * | 12/2014 | Knorr | ............. | B29C 47/92 73/632 |
| 9,273,957 B2 * | 3/2016 | Knorr | ............. | G01B 21/08 |
| 2007/0034008 A1 * | 2/2007 | Voss | ............. | G01N 29/11 73/570 |
| 2007/0285643 A1 * | 12/2007 | Wedowski | ......... | G01B 11/0625 355/67 |
| 2010/0086672 A1 * | 4/2010 | Von Drasek | ............. | B31F 1/14 427/9 |
| 2010/0321047 A1 * | 12/2010 | Zollner | ............. | G03G 15/5037 324/699 |
| 2011/0189378 A1 * | 8/2011 | Moon | ............. | B05C 1/0817 427/9 |

\* cited by examiner

ULTRASONIC TRANSMITTING AND RECEIVING DEVICE FOR THICKNESS AND/OR GRAMMAGE MEASUREMENT

RELATED APPLICATIONS

This application is a continuation-in-part of U.S. patent application Ser. No. 13/431,171 filed on Mar. 27, 2012 which claims the benefit of German patent application number DE 10 2011 015 334.9 filed Mar. 28, 2011, the contents of both are incorporated by reference herein in their entireties.

TECHNICAL FIELD

The invention relates to an ultrasonic transmitting and receiving device for measuring the transmission and/or reflection of an ultrasonic signal on a material sheet (material foil). Based on the transmission and/or reflection measurement, the layer thickness and/or the grammage (mass per unit area) of the material sheet can be absolutely determined.

BACKGROUND

From DE 42 36 436 A1, a measurement method for contact-less determination of the grammage of thin material sheets by means of ultrasonic sound is known. In the method, by means of an ultrasonic transmitter and an ultrasonic receiver, the transmission absorption of an ultrasonic beam upon passage through a material foil is determined in contact-less manner. Based on the absorption and a calibration factor, the grammage is calculated.

From DE 201 09 119 U1, a further device for measuring the thickness of material sheets is known. There, the material sheet is pulled over a roller, wherein a sensor is arranged on a rolling cart moving back and forth over the roller in traversing manner for thickness measurement.

Further ultrasonic sensor arrangements for grammage determination or for grammage comparison are known from DE 103 27 389 B3, DE 199 08 932 A1, DE 10 2005 037 086 A1, DE 203 12 388 U1 and DE 30 48 710 A1.

There is a need for providing an ultrasonic transmitting and receiving device, an arrangement including the device as well as a method, in which the thickness measurement and/or grammage measurement on a material sheet are improved.

SUMMARY

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one implementation, a system or arrangement comprising a thin material sheet producing or coating apparatus and an ultrasonic transmitting and receiving device is provided. The terms "system" and "arrangement" are used interchangeably herein. The ultrasonic transmitting and receiving device is adapted for measuring the transmission T and/or the reflection R of ultrasonic waves on the thin material sheet and is adapted for determining the layer thickness and/or the grammage of the material sheet or of the coating layer on the material sheet using the measured transmission and/or reflection of the ultrasonic waves.

The thin material sheet producing or coating apparatus is configured for producing the thin material sheet or for coating the thin material sheet with a coating layer such as to produce a coated thin material sheet.

The thin material sheet producing or coating apparatus comprises: an elongated nozzle or gap configured to expel the thin material sheet, or a gap member adapted to apply the coating layer onto a surface of the thin material sheet; an actuator adapted to adjust the thickness of the thin material sheet by adjusting the outlet gap width of the elongated nozzle or gap, or adapted to adjust the thickness of the coating layer by adjusting the gap width of the gap member, and a control unit adapted to control the actuator for expelling the thin material sheet with a predetermined thickness or for coating the material sheet with a predetermined coating layer thickness.

The ultrasonic transmission and receiving device comprises: a plurality of ultrasonic transmitters; a plurality of ultrasonic receivers, wherein the number of the ultrasonic receivers corresponds to the number or the two-fold number of the ultrasonic transmitters; and one receiver electronic device respectively for each of the ultrasonic receivers or a group receiver electronic device respectively for a predetermined number of ultrasonic receivers.

The control unit is configured to receive at least one measurement value for the layer thickness and/or the grammage from a control unit of the ultrasonic transmission and receiving device, and the control unit is configured to control the at least one actuator to adjust of alter the outlet gap width of the elongated nozzle or the gap width of the gap member in dependency of the at least one measurement value.

In an embodiment the thin material sheet producing or coating apparatus is a thin material sheet producing apparatus that expels the thin material sheet through an adjustable nozzle gap or through an adjustable gap formed between a roller and a plate or formed between two rollers (for example in case the material sheet is produced using a calender).

In an embodiment the thin material sheet producing or coating apparatus is a calender adapted to coat a material sheet supplied to the calender with a coating film and/or adapted to produce a material sheet. The calender may have at least one pair of cooperating rollers having an adjustable gap there between, wherein the actuator is adapted to set a predefined gap width under the control of the control unit.

In another embodiment the thin material sheet coating apparatus is a screen printing device, a doctor knife or doctor blade coating device, a flexo or pad coating device, a printing device, a sol-gel coating device, a varnishing device, a dip-coating device, a laminating device, a CVD or PVD device, a powder coating device, or a spray coating device. Preferably the thin material sheet coating apparatus has a gap or nozzle element with a gap or nozzle width being adjustable by the actuator under the control of the control unit.

In an embodiment the arrangement may comprise two measuring arrangements, one associated with a thin material sheet producing apparatus and the other measuring arrangement associated with a thin material sheet coating apparatus. For this preferably the arrangement comprises: a first arrangement comprising a first thin material sheet producing or coating apparatus and a first ultrasonic transmission and receiving device; and downstream or in transport direction after the first arrangement, a second arrangement comprising a second thin material sheet coating apparatus and a second ultrasonic transmission and receiving device. Preferably the second arrangement is adapted to coat the thin material sheet or coated material sheet provided from the first arrangement with a coating layer of predetermined thickness.

According to an implementation a method coating a material sheet with a coating of predetermined thickness is provided, wherein the method comprises: supplying a material sheet to a thin material sheet coating apparatus, coating the material sheet with a coating layer in the thin material sheet coating apparatus, determining the thickness/grammage of the coating layer or of the coated material using a measuring unit, calculating the thickness/grammage of the coating layer in a control unit, if applicable after subtracting the known thickness and/or grammage of the material sheet, determining a deviation between the set value and calculated current value for the thickness and/or grammage of the coating layer, and if required, adjusting the thickness and/or grammage of the coating layer applied by the thin material sheet coating apparatus.

In an embodiment the calculating step the thickness and/or grammage of the material sheet is provided by a second measuring unit arranged upstream or in transport direction before the thin material sheet coating apparatus.

According to one implementation, an ultrasonic transmitting and receiving device is provided, by which the transmission and/or the reflection of the ultrasonic waves through or from a thin material sheet are measured by means of the ultrasonic waves. The thickness and/or the grammage (mass per unit area) of the material sheet may be determined based on the measured transmission and/or reflection. The device comprises a plurality of ultrasonic transmitters, wherein each of the ultrasonic transmitters is oriented such that an ultrasonic signal can be emitted towards a thin material sheet. The ultrasonic signal may be a signal pulse or a sequence of signal pulses ("signal burst"). The device unit may include a control unit, by means of which the absolute layer thickness and/or the grammage can be calculated using a calibration value or a calibration curve and the measured transmission and/or reflection and can be displayed and/or output as an absolute value.

An ultrasonic receiver may be associated with each of the ultrasonic transmitters and oriented towards this such that the ultrasonic signal emitted by the associated ultrasonic transmitter can be received. For example, for determining the transmission, the receiver may be arranged on the side of the material sheet opposing the ultrasonic transmitter and oriented towards the ultrasonic transmitter. For example, for measuring the reflection, either a separate receiver may be arranged on the same side of the material sheet as the ultrasonic transmitter, or the ultrasonic transmitter may operate as a transceiver, by which the signal can be both radiated and received.

Dedicated receiver electronics may be associated with each of the ultrasonic receivers, or group receiver electronics may each be associated with a group of ultrasonic receivers, such that parallel processing of the ultrasonic signals received and converted by the ultrasonic receivers can be executed with the receiver electronics or group receiver electronics. Within the group receiver electronics a dedicated electronics unit may be associated with each ultrasonic receiver in the group of the ultrasonic receivers which are associated with the group receiver electronics, such that parallel processing of the received voltage signal converted by the receiver can also be executed for each member of the group.

By the plurality of ultrasonic transmitters, ultrasonic receivers and receiver electronics or group receiver electronics, it is provided to emit, to receive ultrasonic signals and to at least partially condition or process them by the electronics in time-parallel manner. Therefore, it is possible to substantially increase the spatial density and/or the repetition rate of the transmission and/or reflection measurements on the material sheet as compared to for example a reversing system with only one transmitting/receiving unit. Thereby, for example, the quality control by means of thickness and/or grammage determination on a material sheet can be substantially improved. For example, thereby, the fault detection in a material sheet such as a fuel cell membrane, battery membrane or the like increases such that the reject rate is considerably decreased related to the entire production process due to the fault detection of material defects.

The ultrasonic transmitters may be arranged so as to be distributed on a supporting device such that they extend in transverse direction to the material sheet. Thereby, it is no longer required to provide a traversing device moving the ultrasonic transmitters back and forth across the width (transverse direction) of the material sheet. The ultrasonic transmitters may be fixedly arranged, i.e. they are moved neither in transverse direction nor in longitudinal direction to the material sheet, i.e. during the measurements, exclusively the material sheet moves in longitudinal direction. Thereby, the expenses for providing mechanically moving parts are reduced or are completely avoided. In an embodiment, it can be provided that the supporting device for the ultrasonic transmitters is moved over a small transverse stroke, for example a transverse stroke of less than $\frac{1}{10}$, $\frac{1}{15}$, $\frac{1}{20}$ or $\frac{1}{30}$ of the material sheet width.

In an embodiment, the ultrasonic transmitters are arranged so as to be spatially distributed both over the transverse direction of the material sheet and over a predetermined depth in longitudinal direction of the material sheet. By the distribution of the ultrasonic transmitters in longitudinal direction, it becomes possible to achieve the coverage of the measurement points in longitudinal direction of the material sheet with temporal repetition in nearly continuous or even overlapping manner in a clocked, non-continuous measurement even at high sheet longitudinal velocities. Alternatively or additionally, it is possible to increase the resolution of the measurement locations in transverse direction with both transverse and longitudinal offset of the adjacent ultrasonic transmitters such that complete or nearly complete coverage with measurement points in transverse direction is achieved.

Notably, multiple lines of ultrasonic transmitters extending in transverse direction of the material sheet may be provided, wherein all of the ultrasonic transmitters of a line are offset to each other in transverse direction and the lines are offset to each other in longitudinal direction. Therein, the dual offset is advantageous such that with projection of the ultrasonic transmitters in longitudinal direction, thus upon viewing the ultrasonic transmitters in the direction of the running direction of the material sheet, the projection of the ultrasonic transmitters is arranged equidistantly to each other. Therein, viewed in projection and in transverse direction, a uniform sampling density in transverse direction of the material sheet is achieved. In an alternative or additional embodiment, a sequence of the ultrasonic transmitters results in a projection in longitudinal direction such that a repeating permutation of the line number of the associated ultrasonic transmitter arises in projected sequence in transverse direction. (Example for illustration: if the lines and columns result in a skewed array or a skewed matrix $A_{ij}$ of the size 3×3 with the column number i=1, 2, 3 and the line number j=1, 2, 3, then the permutation sequence $a_{11}$, $a_{12}$, $a_{13}$, $a_{21}$, $a_{22}$, $a_{23}$, $a_{31}$, $a_{32}$, $a_{33}$ results in longitudinal projection).

With such an arrangement, the ultrasonic transmitters can be arranged next to each other on a small area in compact manner, while the coverage with ultrasonic transmitters (and the ultrasonic signals radiated by them to the material sheet, respectively) projected in longitudinal direction is provided in transverse direction to the material sheet in continuous or nearly continuous manner.

The ultrasonic transmitters may be arranged such that only each one ultrasonic transmitter is located in longitudinal direction of the moving material sheet, i.e. all of the ultrasonic transmitters are offset to each other in transverse direction. However, this does not mean that the active transmitting surfaces of the ultrasonic transmitters do not overlap in longitudinal projection (see below). If for example two lines of ultrasonic transmitters with ultrasonic transmitters arranged as distributed over the transverse direction are provided and if the two lines are offset in longitudinal direction, thus, advantageously, the ultrasonic transmitters of the second line are arranged offset by half the distance of the ultrasonic transmitters of the first line in transverse direction with respect to the ultrasonic transmitters of the first line. Thereby, in longitudinal projection, each of the ultrasonic transmitters of the second line is located between two ultrasonic transmitters of the first line (except for the last ultrasonic transmitter of the second line).

According to an embodiment, the device includes multiple lines of ultrasonic transmitters arranged to be offset to each other in longitudinal direction, wherein the ultrasonic transmitters of the same column are located on one line in the lines located one behind the other, which is under an angle with respect to the longitudinal direction of the material sheet. In some implementations, the angle of this line is in a range of 10° to 80° to the longitudinal direction, or in other implementations in a range of 20° to 70°, 30° to 60° or 40° to 50°.

Each of the ultrasonic transmitters may have an active transmitting surface extending both in longitudinal direction and in transverse direction. In some implementations, the transmitting surface of the ultrasonic transmitters is round or elliptical. In an embodiment, the ultrasonic transmitters are arranged such that in projection of the ultrasonic transmitters in longitudinal direction of the material sheet, the transmitting surfaces of the ultrasonic transmitters lying next to each other in transverse direction overlap. Thereby, seamless coverage of the sampling of the material sheet in transverse direction in projection is achieved. In some implementations, the overlapping degree between each two ultrasonic transmitters adjacent in projected transverse direction is at least 10% in transverse direction of the projected transmitting surface, or in other implementations at least 15%, 20%, 30%, 35% or 40%.

In some implementations, 100% of the sheet width is covered by means of the ultrasonic transmitters or the ultrasonic beam emitted by the ultrasonic transmitters, and in some implementations at least partially overlapping coverage in transverse direction of the material sheet is achieved.

A sensor unit of the device is composed of an ultrasonic transmitter and one or two ultrasonic receivers associated with the ultrasonic transmitter (two receivers in case of the simultaneous measurement of transmission and reflection). The radiating direction of the ultrasonic signal from the ultrasonic transmitter towards the surface may be perpendicularly or approximately perpendicularly oriented to the material sheet. The receiver of the sensor unit therein may be oriented such that it is arranged opposing the ultrasonic transmitter with respect to the material sheet in transmission and receives the transmitted signal. Alternatively or additionally, the ultrasonic receiver measuring the reflection is arranged on the same side of the material sheet as the ultrasonic transmitter. The ultrasonic receiver may at the same time be the ultrasonic transmitter.

If both transmission and reflection are measured, then in some implementations, one dedicated receiver electronics is provided for each of the reflection receivers and transmission receivers or one group electronics is provided each for a group of reflection receivers and transmission receivers. The described parallel processing of the received signals therein relates to both the transmission and the reflection signals. In the processing or calculation the quotients of the transmission and reflection signals may each be processed for each sensor unit (transmitter and associated transmission and reflection receivers) (quotient either T/R or R/T).

In an embodiment, the ultrasonic receivers are arranged on a second supporting device paired to the arrangement of the ultrasonic transmitters on the first supporting device. In transmission measurement, the second supporting device may be arranged on the side of the material sheet opposing the first supporting device for the ultrasonic transmitters. By the arrangement of the receivers on a common, second supporting device, all of the receivers can be collectively oriented to the ultrasonic transmitters such that individual orientation of each receiver to its associated transmitter is not required.

Each of the receiver electronics or group receiver electronics may include an amplifier, in which the amplification is adjustable. In particular, each of the amplifiers may be adjustable in multiple amplification stages and/or the amplification of each of the amplifiers is individually, but centrally adjustable under control of a main control unit via the control or programming of the main control unit. By means of the adjustable amplification, the basic amplification for the amplification of the received ultrasonic signal converted to a voltage signal can be calibrated for each of the ultrasonic receivers. Thereby, for example, an amplification of the received signal is adjusted such that the same signal (for example same signal amplitude and/or signal voltage) is present with all of the amplified signals on identical measurement conditions. Such a uniform or identical measurement condition for example exists if no material sheet is provided between transmitter and receiver or in reflection arrangement towards the radiated signal such that a basic signal in air (transmission signal/reflection signal against air) results in a uniform signal strength after amplification. In some implementations, even when using the group receiver electronics the amplification is also individually adjustable for each individual ultrasonic receiver of the group. Thereby, differences in the transmitting strength of the ultrasonic transmitters, the receiver sensitivities of the signal receivers or different attenuations on the signal paths can be normalized.

The receiver electronics or the group receiver electronics may have a microcontroller, in particular a microcontroller, by which or in which the amplification of the amplifier of the receiver electronics is adjustable. This correspondingly applies to the group receiver electronics. Here too, the amplification again may be individually and independently adjustable for each of the ultrasonic receivers of the group.

Alternatively or additionally, each of the receiver electronics or the group receiver electronics includes a signal processor for evaluating the signal or signals received by the associated ultrasonic receiver or the group of ultrasonic receivers. With the signal processor, it is possible to provide signal processing on the level of the receiver electronics or group receiver electronics such that parallel processing is implemented. The signal processor in the group receiver electronics may have a processing speed for processing the signals of the ultrasonic receivers of the group in parallel or sequentially. For example with clocked measurement the evaluation or calculation for each receiver of the group is terminated before a new measurement clock begins. Alternatively, a dedicated signal processor is provided or implemented for each of the receivers of the group in the group receiver electronics.

A main control unit may be provided, by means of which a transmit signal can be generated, which is supplied to each of the ultrasonic transmitters via a bus line or parallel lines. In particular the signal generation and signal transmitting connection between the main control unit and the ultrasonic transmitters is such that the ultrasonic transmitters radiate the ultrasonic signal at the same time or with a slight temporal offset. If a temporal offset is present, then in clocked measurement operation the period of time between the earliest ultrasonic signal emitted by one of the ultrasonic transmitters to a time, at which the last ultrasonic transmitter emits the signal in the same measurement clock, is smaller than the propagation time of undesired sound reflections and/or propagation times between an ultrasonic transmitter and a signal receiver not associated with this ultrasonic transmitter (i.e. from an ultrasonic signal passing between different sensor units).

Besides the ultrasonic transmitter and receiver pairs, a measuring group (in the following also referred to as a "sensor unit") with at least one signal transmitter and a signal receiver may be associated with the device, by which the layer thickness and/or the grammage (mass per unit area) of the material sheet can be determined during a reversing movement or reciprocation of the measuring group transversely to the material sheet. In the sensor unit, a sensor for detecting transmission and/or reflection values of the material sheet is movable in transverse direction of the material sheet transported in longitudinal direction. The sensor unit can be moved back and forth in traversing manner along the device (for example between the outer longitudinal edges of the material sheet) by means of a drive unit. Thereby, for example, during a production process of the material sheet, the transverse distribution of the layer thickness and/or the grammage is monitored (e.g. along a zigzag-shaped measuring path along the material sheet).

The device may include a sensor calibration position, in which the sensor unit is moved out of the material sheet measuring section. In the sensor calibration position, a supporting device with a calibration sample (as a calibration standard) is arranged. In the sensor calibration position, the sensor is moved relatively to the calibration sample and/or the calibration sample is moved relatively to the sensor by means of a drive.

In an embodiment, a rotation and/or linear movement is effected by means of a rotation and/or linear drive, which moves the calibration measurement sample retained in the supporting device relatively to the sensor. Additionally or alternatively in the sensor calibration position the sensor can be moved over the calibration sample retained in the supporting device planar or at least in a linear direction, which in some implementations is preferably in the transverse direction of the material sheet.

The sensor unit may include an ultrasonic sensor unit, in which the measurement signal for layer thickness and/or grammage determination is an ultrasonic pulse. Alternatively, an optical sensor is used, which for example uses a laser beam or a light emitting diode beam. Further alternatively, the sensor unit may have a ray sensor emitting and receiving gamma or beta rays.

In an embodiment, the sensor unit is exclusively constructed as a transmission unit, in which only the absorption in transmission of the sensor signal through the material sheet is determined. Or the sensor unit is exclusively a reflection unit, in which the reflection of the measurement signal from the material sheet or from the backside of the material sheet is detected. Or alternatively, the sensor unit is a combined transmission and reflection measurement unit, in which both the attenuation of the sensor signal in reflection and in transmission are determined. In such a transmission and reflection measurement, one of the values can be used for plausibility check of the other value and/or for averaging in the layer thickness and/or grammage determination.

The sensor unit may be used for calibration of the plurality of the ultrasonic transmitter and receiver pairs of the device and/or the sensor unit may be calibrated in the sensor calibration position with the calibration sample.

According to another implementation, an arrangement includes a device according to one of the preceding embodiments and an extruder, in which an actuator of an extrusion die of the extruder is adjustable depending on the layer thickness and/or grammage measurement of the device. Thereby, control of the layer thickness or of the grammage in the manufacture of a material sheet, for example a foil sheet, is provided.

According to another implementation, an ultrasonic transmitting and receiving device with a plurality of sensor units is used, wherein each sensor unit is formed of an ultrasonic transmitter and an ultrasonic receiver associated with it. The device may be formed as above described, i.e. the above described elements can also be used individually or in any combination with each other in the device for the method.

In the method, a control signal is supplied to all of the ultrasonic transmitters at the same time or with a little temporal offset within a time window such that the ultrasonic transmitters emit their ultrasonic signal at the same time or within the time window. The time window is dimensioned such that a spurious reflection signal and/or a signal of another ultrasonic transmitter is not received by an ultrasonic receiver associated with the ultrasonic transmitter in a corresponding time window of the measurement of the ultrasonic signal. By the simultaneous or nearly simultaneous transmission of the ultrasonic signal, parallel measurement of all sensor units is provided, wherein at the same time cross-talk between the sensor units or an error signal by reflection within the measuring section of a sensor unit is excluded.

Furthermore, in the method, a parallel or substantially parallel processing is provided, wherein one receiver electronics is associated with each of the ultrasonic receivers or one group receiver electronics is associated with a group of ultrasonic receivers, by which evaluation or pre-processing of the signals of the ultrasonic receivers can be executed in parallel or substantially in parallel. Using the group receiver electronics the processing may also be effected for all of the signals of the receivers associated with the group or by fast electronics such that in a clocked measurement the processing result for all of the receivers of the group is finished before the next measurement clock occurs.

The evaluated or pre-processed signals may be supplied to the receiver electronics or the group receiver electronics of a main control device. Evaluation of the signal for determining the thickness and/or grammage determination may be effected either already on the level of the receiver electronics or group receiver electronics or in the main control device after forwarding the pre-processed signals to the main control device.

Thereby, by means of the method, both parallel emission (multiple measurement positions on the material sheet at the same time) and parallel processing of the signals is provided such that an intensive detection of the thickness and/or the grammage of a material sheet is provided with high density and repetition rate.

In an embodiment, the sensor units are calibrated by measuring a basic sensitivity based on a signal transmitted through the air (thus without material sheet). This value may be used in determining the sensitivity in order to adjust an amplification factor individual to the transmitting unit in the receiver electronics or group receiver electronics such that a receive signal is obtained after amplification with identical conditions on the measuring section, which has the same size or strength normalized for all transmitting units.

Alternatively or additionally, a calibration and detection of a conversion factor between transmission value and/or reflection value and association with a thickness and/or a grammage of a material sheet is effected by using the calibration at a calibration sample or calibration standard, which is applied between the sensor units such that measurement on a material sheet is simulated. After removal of the calibration sample a corresponding material sheet to be measured can then be interposed between the sensor units, the measurements on the material sheet can be carried out and the thickness and/or the grammage can be assigned by means of the previously determined calibration value.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

DETAILED DESCRIPTION

Figure 1:
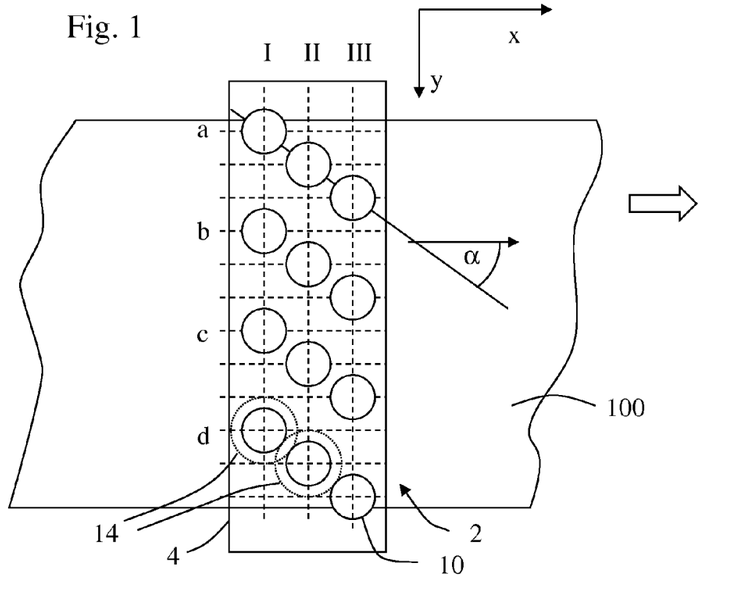
FIG. 1 is a schematic plan view of a measuring unit for measuring the grammage of a material sheet.

FIG. 1 shows in schematic plan view a measuring unit 2 for thickness measurement and/or grammage determination at a material sheet 100. In the measuring unit, a plurality of ultrasonic transmitters 10 and an equal number of ultrasonic receivers 12 in the form of an array are arranged planar above the material sheet (in the illustrated example, the ultrasonic transmitters 10) and below the material sheet (in the illustrated example, the ultrasonic receivers 12). For simplicity, the transporting device for moving the material sheet 100 forward in the longitudinal direction x thereof is not represented. In the figures, the size ratios and distance ratios are not represented to scale, but are presented such that they serve for explaining the invention.

Figure 2:
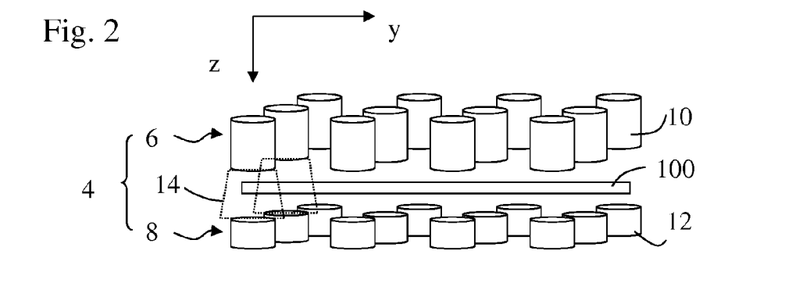
FIG. 2 is a schematic side view of the ultrasonic transmitters and receivers of the measuring unit above and below the material sheet.

FIG. 2 shows in schematic and partially perspective representation the distribution of the ultrasonic transmitters 10 and the ultrasonic receivers 12 arranged correspondingly opposite and coaxial to each of the ultrasonic transmitters.

Figure 3:
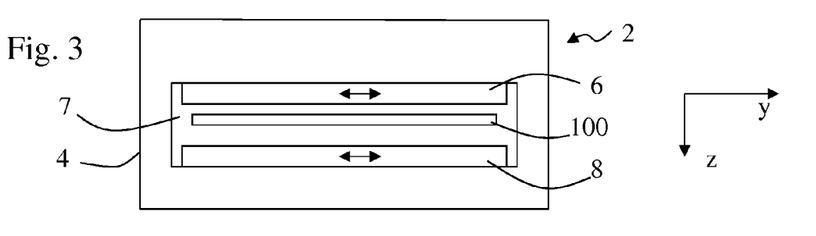
FIG. 3 is a schematic side view of the measuring unit with the transmitting block arranged above the material sheet and the receiving block arranged below the material sheet.

FIG. 3 shows in schematic lateral view of a portal 4 of the measuring unit 2 with an upper transverse beam and a lower transverse beam as well as the lateral pillars, which together leave open a slot 7 extending in x direction through the portal 4. The material sheet 100 is transported in x direction through the slot 7. The portal and thus the array arrangement extends transversely, thus in y direction, to the material sheet 100.

FIG. 1 indicates by means of the circles, which represent the ultrasonic transmitters 10, how the ultrasonic transmitters form three lines I, II and III, wherein each line is offset in x direction to the preceding one. The columns of the array are formed by the columns a, b, c and d. The ultrasonic transmitters 10 are not on a straight line in x direction, but are arranged offset to each other in an angle $\alpha$ to the x direction. An ultrasonic receiver 12 is oriented coaxially in z direction to each of the ultrasonic transmitters 10. Thus each one of the ultrasonic sensors is formed by one of the ultrasonic transmitters and one paired ultrasonic receiver, which is arranged in the direction of the normal perpendicularly to the center of the sound emitting surface of the ultrasonic transmitter. I.e. in a sensor, the center of the receiving surface of an ultrasonic receiver 12 is oriented coaxially to the axis of a transmitter 10. Thereby, a pairing of ultrasonic transmitter and ultrasonic receiver respectively results, wherein 4×3=12 ultrasonic transmitting/receiving pairs are provided in the example illustrated in the figures.

Both the number of the lines I, II and III and the number of the columns a, b, c, d can be selected differently depending on the material sheet width and the desired overlap or the distance of the measurement regions (see below). The ultrasonic transmitters 10 are mechanically supported distributed in planar manner on a transmitting block 6, wherein the transmitting block 6 in turn is mounted on the upper transverse beam of the portal 4. Furthermore, FIG. 3 shows a receiving block 8 below the material sheet 100 on which the ultrasonic receivers 12 are supported distributed in planar manner, wherein here the receiving block 8 is mounted on the lower transverse beam of the portal 4. In an embodiment, it can be provided that both the transmitting block 6 and the receiving block 8 are displaced synchronously with each other in reversing manner in transverse direction (y direction), while the material thickness or the grammage is measured. By this optional transverse displacement it is effected that the non-uniform signal distribution of the ultrasonic signal is drawn over various "tracks" in x direction of the material sheet in a temporally varied manner. In a synchronous, harmonic transverse displacement of the blocks 6, 8, thus, there results a sinusoidal extension of the measurement points in x direction of the material sheet. The reversing, synchronous displacement of the blocks 6, 8 is effected such that the coaxial orientation of the ultrasonic transmitters 10 to the ultrasonic receivers 12 is maintained. However, the blocks 6 and 8 are preferably rigidly supported on the portal 4 or on a frame of the measuring unit 2.

In the schematic side view of FIG. 2 and the plan view of FIG. 1, the extension of the main intensity cone 14 of an ultrasonic signal distribution is illustrated. Therein, the signal lobe 14 illustrates the lateral divergence of an ultrasonic wave of the ultrasonic signal, which is radiated from an ultrasonic transmitter 10. The diameter of the lobe 14 is greater than the diameter of the radiation surface of the ultrasonic transmitter 10 on the level of the receiving surface of the ultrasonic receivers 12. As indicated by means of the dotted circles 14 in FIG. 1, the distance between the adjacent ultrasonic transmitters 10 is selected such that each ultrasonic receiver 12 substantially only receives the main intensity of the ultrasonic signal of the ultrasonic transmitter 10 associated with and opposing it. Thereby, interferences or cross-talk of a transmitter/receiver pair with the other transmitter/receiver pair (between the sensors) is minimized.

The angular offset a of the transmitter/receiver pairs of the columns relative to the x direction allows performing the grammage determination in y direction in at least a partially overlapping manner such that in ideal case the thickness and/or grammage distribution of the material sheet 100 over the entire width of the material sheet is possible at each time. This arrangement thus substantially differs from that known from the above cited DE 201 09 119 U1, in which—due to the traversing operation of the ultrasonic transmitter—the detection of a material sheet defect (thickness and/or grammage deviation) rather is left to the statistical coincidence than a systematic measurement as it is allowed with the present invention.

Figures 4, 5, 6:
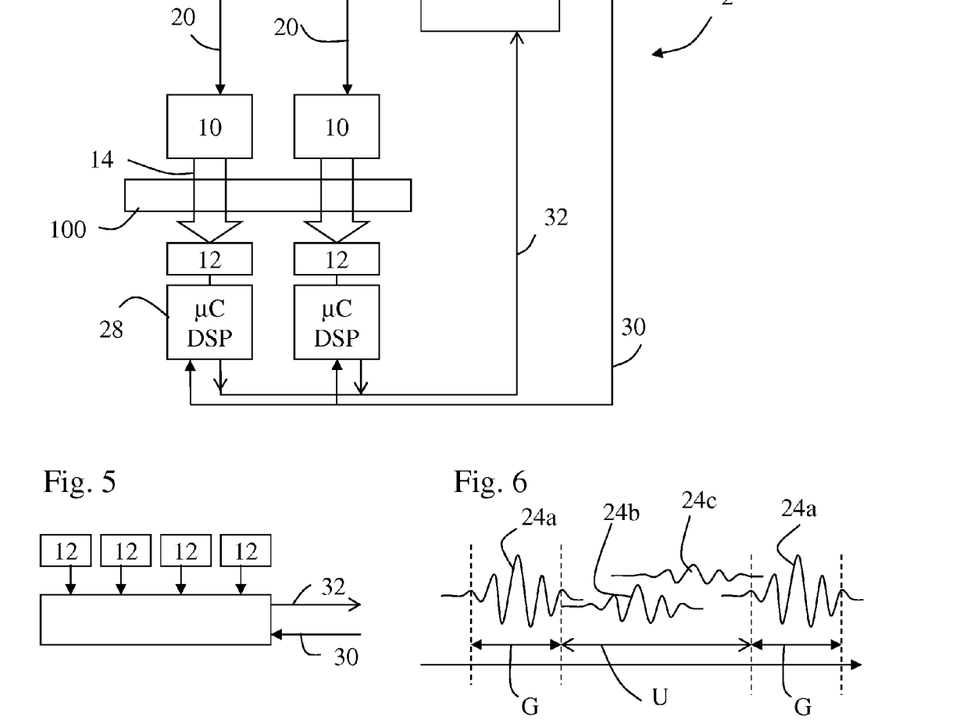
FIG. 4 is a block diagram of the transmitting, receiving and control unit of the measuring unit.
FIG. 5 schematically shows a group of ultrasonic receivers and the group controller associated therewith.
FIG. 6 is a time diagram with received signals and measurement time windows.

FIG. 4 shows in block diagram manner the construction of the measuring unit 2. Here, only two of the ultrasonic transmitters 10 and ultrasonic receivers 12 are exemplarily illustrated. The ultrasonic signal 14 propagates from the transmitter 10 towards the material sheet 100, passes it with attenuation of the intensity of the signal, which impinges on the receiving surface of the receiver 12 after exiting on the bottom of the material sheet. In each measurement interval (time window G in FIG. 6), the signal illustrated as a signal sequence 24 in FIG. 4 is supplied to each transmitter. The signal sequence 24 is generated in a main control unit 22 and supplied to the ultrasonic transmitters 10 in parallel or simultaneously via a transducer 18.

The ultrasonic signal 14 converted into an electrical signal by the ultrasonic transducer of the ultrasonic receivers 12 is supplied to a receiver controller 28. A dedicated controller 28 is associated with each ultrasonic receiver 12. The electrical signal is processed by means of a digital signal processor in the receiver controller 28 such that just on the level of the controllers 28 signal pre-processing is executed. The signal processing may be effected by means of corresponding calibration values such that the controllers 28 may output a signal value corresponding to the material thickness or the grammage to the control unit 22 via a receive signal line 32. Thereby, the main control unit 22 is relieved from the individual signal conditioning or processing and only statistical and control tasks have to be executed by the control unit 22. By the parallel processing in the controllers 28 respectively associated with a receiver 12, a parallel processing is provided, which together with the planar distribution of the sensor units 10, 12 in the array allows a nearly complete "in situ" monitoring of the material quality of the material sheet 100. Even in fast production processes for the material sheet, thereby, high-speed quality monitoring of high density is made available such that high-quality material sheets (such as electrolyte membranes, fuel cell membranes or high-performance battery isolator foils or membranes) can also be produced and the quality thereof can be monitored online.

FIG. 5 shows a further embodiment, in which a group controller 29 is provided for each four receivers 12 instead of each one controller 28 per receiver 12. In the 3×4 array of FIG. 1, then, three group controllers 29 are used instead of twelve individual controllers 28. The group controllers have a dedicated amplifier component with individual amplification for each receiver 12 belonging to the group. By means of the signal processor DSP of the group controller 29, the signals of the associated receivers 12 are evaluated sequentially one after the other, but with such a velocity that the computing result is available and output before the next measurement interval begins. With respect to FIG. 6 this means that the result of the signal evaluation of all of the associated receivers 12 is transmitted to the main control unit before the next time window G starts (the evaluation period of time is thus shorter than the sum of the periods of time G and U). Programming of the amplification, the supply of the supply voltage(s) of the controller 29 and programming of the signal processor DSP of the controller 29 are effected via the control line 30 coming from the main control unit 22. The evaluation signals of the controller 29 are supplied to the main control unit 22 via the line 32.

The time diagram of FIG. 6 illustrates the voltage signal at the output of the receivers 12. The measurement is performed with the repetition rate 1/(G+U), thus also with this rate, the signal sequence 24 is output to the transmitters 10. Therein, G is the time window or the time gate, in which the received signal 24a is evaluated in order to determine from it the thickness and/or the grammage of the material sheet by means of the DSP. U is a time interval or a period of time, during which the ultrasonic signal is not received and processed. The duration of G is dimensioned such that the evaluation can be performed with an error as low as possible (multiple wave trains after excitation with the pulse burst 24). The duration of U is dimensioned such that undesired spurious signals are masked in this time. Here, exemplarily illustrated spurious signals are a reflection signal 24b, which arises in that the signal radiated from the transmitter surface is partially reflected on the material sheet surface, returns to the transmitter surface, is again reflected there and again passes the material sheet and is recorded by the receiver 12 with corresponding propagation time delay. A further spurious signal 24c arises in that the transmit signal is radiated by a transmitter 10 laterally towards an adjacent receiver 12 and there in the adjacent receiver induces a signal 24c which is propagation time-delayed but weaker.

Figure 7:
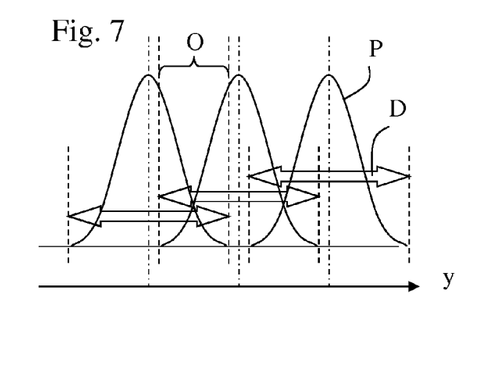
FIG. 7 is a set of intensity profiles of the ultrasonic signals emitted by the ultrasonic transmitters in projection.

FIG. 7 shows in x projection the ultrasonic signal intensity extending in y direction until it results by the array of the transmitting/receiving pairs across the width of the material sheet. In FIG. 7, for simplicity, only 3 of the overall 12 intensity curves P are illustrated. Therein, the intensity P is that of one transmitter 10, respectively. Therein, the intensity curve is approximately Gaussian, and with respect to the z axis there is rotational symmetry of the intensity distribution because the ultrasonic transmitting surfaces are round and radiate in rotationally symmetric manner.

As is apparent from FIG. 7, the maximum diameter ranges of the diameter D of the radiation surfaces of the ultrasonic transmitters 10 overlap in x projection such that an overlapping region O results in the transmitter 10 closest in y direction. Thereby, the measurement intensity P of all transmitters 10 never drops to 0 in the extension of the y direction, and in transverse direction (y direction) of the material sheet 100, a width region does not arise, which is not covered by the measurement or the ultrasonic signal. Therefore, due to the array and the columns of the array arranged in an angular offset, a dead zone in transverse direction of the material sheet does not arise.

Figure 8:
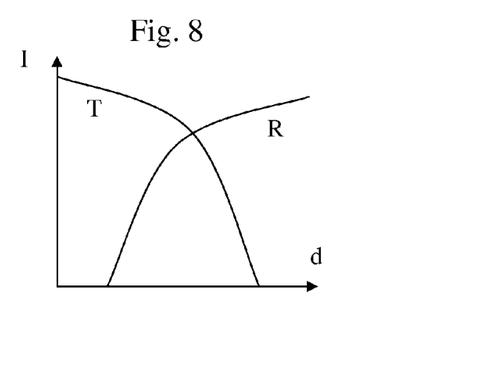
FIG. 8 is a plot of the intensity of the ultrasonic signal in transmission and reflection depending on the thickness of the material sheet.

FIG. 8 schematically shows the intensity curve of an ultrasonic signal in transmission T and in reflection R depending on the thickness d of the material sheet. Based on such calibration curves for an ideal material sample the thickness or the grammage can be determined based on the actually measured signal variation. In the illustrated arrangement, measurement is made in transmission such that the curve T is used in the thickness or grammage determination.

For example, if a thicker or thinner material sheet would result in an intermediate region between the intensity maxima of the intensity curve P of two transmitters 10 adjacent in y direction in the material sheet to be measured due to a systematic production fault, thus, this systematic fault can be identified either by detecting systematically a deviating value in the two concerned transmitter/receiver pairs 10/12. Or, alternatively, as described in connection with FIG. 3, the transmitting block and the receiving block 6, 8 are displaced synchronously with a short y stroke in y-direction such that the measurement sensitivity is shifted towards maximum of the intensity curve P with such a systematic fault.

Figure 9:
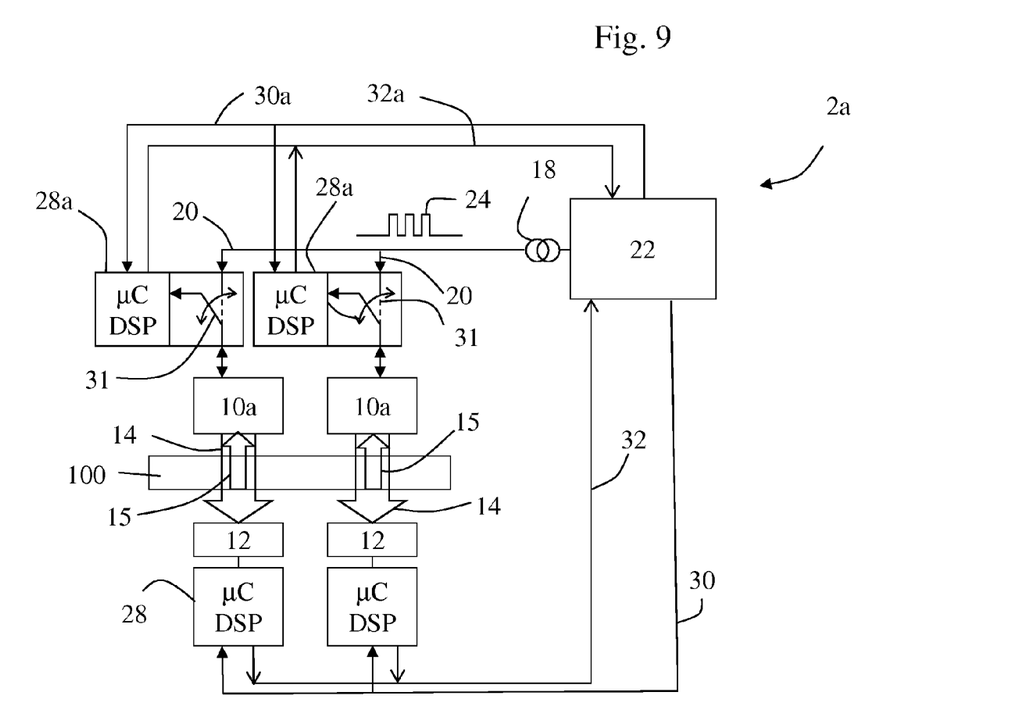
FIG. 9 is a block diagram of the transmitting, receiving and control unit in further embodiment of the measuring unit.

FIG. 9 shows a further configuration of the measuring unit 2 as a measuring unit 2a. Identical, same or equivalently acting elements of the measuring unit 2a are labeled with the same reference characters or with reference characters supplemented with the addition "a" as the corresponding element of the measuring unit 2. In the measuring unit 2a, the reflection signal 15 reflected back from the material sheet 100 towards the ultrasonic transmitter 10 can also be evaluated or is evaluated with respect to the reflection R (cf. FIG. 8).

The unit 2a allows the following measurement modes: transmission measurement, reflection measurement, transmission and reflection measurement and additionally to these or alternatively to these a propagation time measurement for direct thickness calculation.

With respect to the transmission measurement, the setup is as described above with respect to FIGS. 1 to 8. For reflection measurement, the ultrasonic transmitter 10a operates as a transceiver receiving the ultrasonic signal 15 reflected on the material sheet 100 and converting it into a voltage signal. First, the signal sequence 24 generated by the main control unit 22 is supplied to the receiving controllers 28a modified with respect to the receiving controllers 28. During the transmit interval of the signal sequence 24, a switch 31 provided at each receiving controller 28a connects the input of the line 20 to the input on the respective ultrasonic transmitter 10a such that it operates like the ultrasonic transmitter 10 in this phase and radiates an ultrasonic signal 14 towards the material sheet 100. After the end of the signal sequence 24, the switch 31 connects the ultrasonic transmitter 10a to the microcontroller µC+DSP at the receiving controller 28a. Therein, the converted reflection signal 15 is supplied to the microcontroller and the signal processor thereof for evaluation. Concerning the evaluation and the temporal gating of the reflection receive signal, the above described in communication with the measuring unit 2 for evaluation of the transmission signal applies.

Here, the adjustment of the amplification individually programmable for each receiving controller 28a and the calibration are correspondingly applicable, wherein it applies to the reflection signal instead of the transmission signal. If transmission and reflection are measured at the same time, the receiving controllers 28 and 28a operate in parallel as it was described above for the operation of the receiving controllers 28. The results of the evaluated signals or the pre-processed signals are supplied to the main control unit 22 via the line 32a. Programming, control and current supply of the receiving controllers 28a as well as switching of the switches 31 is effected from the main control unit 22 via the control line 30a.

In an embodiment, instead of individual receiving controllers 38a, a group controller can be used, which is configured analogously to the group controller 29 of FIG. 5. The switch 31 can be a controllable switch, which connects the transmitter 10a to the microcontroller/DSP or to the signal line 20 according to control. Or the switch 31 can be a unidirectional direction gate passing signals 24 incoming from the line 20 towards transmitter 10a and supplying returning signals from the transmitter 10a to the microcontroller.

In evaluation or processing of the signals for thickness and/or grammage determination, the quotient of the values of transmission and reflection (T/R) can be used in the calculation in the measuring unit 2a. Via the quotient formation, measurement errors affecting proportionally or approximately proportionally both the transmission and the reflection are cancelled out. Examples of the cause of such measurement errors are the air temperature, air pressure or air humidity.

If thick or highly absorbing materials are measured as the material sheet, the reflection measurement can provide the more accurate results. For example, in transmission, a thickness measurement is unfavorable if the material thickness approaches to $\lambda/4$ of the wavelength of the ultrasonic sound or exceeds this value. In the reflection signal, it is also possible to determine the thickness of the material sheet 100 directly from the propagation time difference of the reflection signal. The propagation time difference is the difference between the first reflected signal arising upon impinging of the signal 14 on the surface of the material sheet, and the last (without regard to multiple reflections) reflected signal occurring after passage of the signal 14 through the material sheet on the second surface or exit surface. With known sound velocity in the material, then, the material thickness can be directly determined via the propagation time difference determined by means of signal evaluation.

Figure 10:
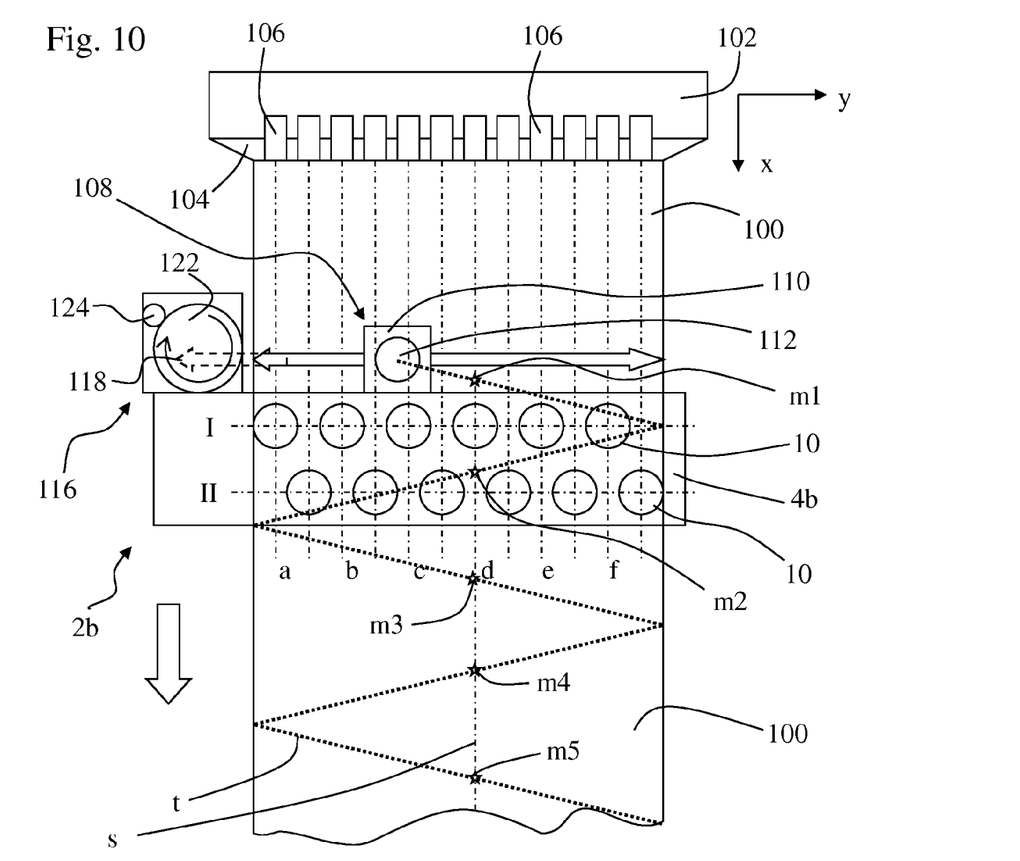
FIG. 10 is a schematic plan view of a measuring unit according to further embodiment with a calibration station and a traversing sensor unit in an arrangement with a foil extruder.

FIG. 10 schematically shows in plan view a further configuration of a grammage measuring unit 2b arranged on a material sheet 100 advanced in longitudinal direction x. In the following, the same reference characters are used for the same or equally acting elements as for the above described embodiments of the measuring units 2, 2a. Unless otherwise mentioned, the above explanations also apply to the measuring unit 2b. As above, for simplicity, the transporting device for advancement of the material sheet 100 is not illustrated. The material sheet is directly measured during the manufacturing process with the measuring unit 2b (also 2 or 2a). As illustrated, the material sheet 100 is extruded as a foil through a flat extrusion die 102 of a foil extruder. In FIG. 10 the further elements of the foil extruder are not illustrated—except for the control unit 101 of the extruder in FIG. 11. Instead of the flat extrusion die, a round extrusion die can also be employed for the foil extruder, wherein after extrusion the material sheet is stretched to a flat material sheet in the transport, before it enters the portal 4b of the measuring unit 2b.

As noted above, the grammage measuring unit 2b has a transverse portal 4b as the basic component, which extends above and below the material sheet 100 across the full width of the material sheet. In this case, the transverse portal 4b extends on one side considerably beyond the sheet width, since a standby and calibration station 116 for a traversing or reciprocating measuring group or sensor unit 108 is additionally arranged laterally to the material sheet. On the upper transverse beam of the transverse portal 4b (cf. arrangement of FIG. 3, the beam extending at the top in y direction), a carriage console 110 is supported on a carriage not visible in the figure, wherein the carriage is movable transversely (thus in y direction) to the material sheet 100 in reversing manner by means of a linear drive.

The carriage console 110 supports a transmitting head 112, which can be moved across the full width of the material sheet 100 by means of the carriage console 110. The carriage console 110 supports the transmitting head 112 radiating ultrasonic pulses to the top of the material sheet for measuring. The ultrasonic signal propagates under attenuation through the material sheet 100 to the lower side thereof, where the attenuated ultrasonic signal exits and impinges on a receiving head 114 opposing the transmitting head 112. The receiving head 114 is arranged on a carriage console not illustrated, which in turn is movable on the lower beam of the transverse portal 4b (cf. FIG. 3). The lower carriage with the carriage console for the receiving head 114 is moved synchronously with the upper carriage with the console 110 such that the transmitting head 112 and receiving head 114 of the measuring group 108 oppose each other at any time in moving along the material sheet and in the standby and calibration station 116 (with the material sheet 100 or the calibration sample 122 in between).

At the extrusion die 102, the thickness of the material sheet is adjusted by means of the pivotable die lip 104, wherein the adjustment is effected by means of actuators 106 arranged equidistantly to each other transversely to the sheet width. The actuators 106 are for example thermal expansion bolts, the longitudinal expansion of which is adjustable by temperature variation such that they adjust the work angle of the die lip 104 by the length variation. Therein, each actuator 106 acts locally in its width region such that the thickness of the material sheet in the corresponding y width range is substantially determined by the actuator 106 in this width range or in intermediate ranges between two adjacent actuators 106 by the cooperation of these two actuators.

At the measuring unit 2b, ultrasonic transmitters 10 and ultrasonic receivers 12 paired thereto are arranged over the width of the material sheet on the portal 4b, the common measurement regions of which cover the full width of the material sheet. The arrangement is as described above, wherein here the transmitting block 6 with the transmitters 10 and the receiving block 8 with the receivers 12 are preferably stationary supported on the portal 4b. In this implementation, two array lines I, II offset to each other in transverse direction (y) and six array columns a-f are provided. The above mentioned relating to the transmitters 10 and receivers 12, the electronic control and evaluation thereof (cf. FIGS. 4 and 9) as well as to the procedure of transmitting/receiving/evaluating correspondingly applies.

Figure 11:
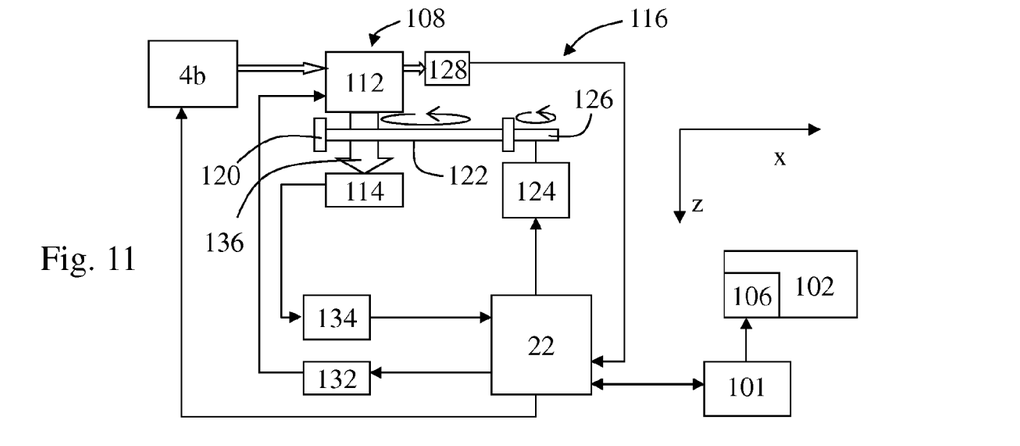
FIG. 11 is a schematic representation of the measuring and control arrangement when positioning the traversing sensor unit in the calibration station of FIG. 10.

As is apparent based on the dot-dashed lines in sheet longitudinal direction (x direction), within the measuring array of the measuring unit 2b one transmitting/receiving pair 10, 12 per actuator 106 is arranged in the longitudinal direction of the sheet 100. The distance of the actuators is in the range of 20 to 40 mm or 25 to 35 mm, typically it is 25.4 or 30 mm. Correspondingly, the center distance of the pairs 10/12 in y direction is equal to the distance of the actuators 106. Here, the association is exemplary from left to right, wherein the transmitting/receiving pair 10/12 in line I and column a is associated with the leftmost actuator 106 and the transmitting/receiving pair 10/12 in line II and column f is associated with the rightmost actuator 106. By this association, it is provided that the measurement results of the layer thickness and/or grammage determination are transmitted from the main control unit 22 to the control unit 101 of the extrusion device as illustrated in FIG. 11. The adjustment of each individual one of the actuators 106 by means of the extruder control unit 101 can then be effected depending on which value of the thickness and/or of the grammage the associated transmitter/receiver pair 10/12 provides. The adjustment of the actuators 106 may be effected continuously and in the form of a feedback control arrangement.

In the schematic cross-sectional view of FIG. 11, the arrangement of transmitting head 112 and receiving head 114 of the measuring group 108 is illustrated in lateral view, wherein the y direction is perpendicular to the drawing plane in FIG. 10 in the lateral view. By 136 an ultrasonic transmission beam is graphically illustrated, which emanates from the transmitting head 112. In the illustrated parking position 118 of the measuring group 108, the transmission beam 136 passes through a calibration sample 122 and impinges on the receiving head 114.

The standby and calibration station 116 is laterally offset to the material sheet, thus offset in y direction or transverse direction to the material sheet 100. The standby and calibration station 116 comprises the parking position 118, in which both the transmitting head 112 and the opposing receiving head 114 are parked during measurement interruptions or for calibration of the measuring group 108 with the transmitting/receiving unit 112, 114.

In the standby and calibration station 116, a clamping ring 120 is rotatably supported, which is set into rotation on its outside by means of a pinion 126. As apparent from FIG. 11, the pinion or gear 126 is driven by a drive motor 124. The pinion 126 engages with a ring gear formed at the outer side of the clamping ring 120 such that the rotating speed or angular position of the clamping ring 120 can be controlled by means of the motor 124. The calibration sample 122 is clamped in the clamping ring 120. The calibration sample 122 is a round blank of a standard material to be employed for calibration. The blank has an area of a square centimeter such that the grammage of the standard can be determined in simple manner by weighing the blank on precision weighing machine. The calibration standard in form of the calibration sample 122 represents a set value for the thickness and/or the grammage of the material sheet 100 and is employed for repeated calibration of the measuring group 108 including the transmitting and receiving heads 112, 114.

FIG. 11 shows the relative position of the calibration sample 122 besides the schematic lateral view of the transmitting and receiving head 112, 114. Similarly, the control and monitoring electronics for the grammage measuring unit 2b relating to the measuring group 108 and calibration station 116 is illustrated in the form of a block diagram. The control of the measuring group 108 and the calibration station 116 is effected by the same main control unit 22, which also provides the control, supply and read-out of the transmitting/receiving units 10/12 of the arrays of the measuring units 2 or 2a. In the unit 2b, the control unit 22 additionally provides the current supply, control, pulse triggering and signal read-out for the measuring group 108 and calibration station 116.

In the standby and calibration station 116, by means of a position sensor 128, it is detected whether the transmitting head 112 and the receiving head 114 have arrived at the correct parking position 118 in order to perform the calibration for example. The position sensor 128 reports its signal to the control unit 22 of the grammage measuring unit 2b. The control unit 22 controls a transmitter controller 132 of the measuring group 108. For example, the transmitting controller 132 obtains the supply voltage and an amplification adjusting signal for adjusting the signal amplification from the control unit 22. With the preset signal amplification, a pulse signal also received from the control unit 22 for the transmitting head 112 is amplified. The transmitter controller 132 outputs the amplified pulse signal to the transmitting head 112, which converts the voltage signal into the ultrasonic signal 136.

The ultrasonic signal received at the receiving head 114 is converted into an electric signal and supplied to a receiver controller 134. The receiver controller executes signal conditioning and passes the conditioned receive signal to the control unit 22. For example, the receiver controller 134 comprises a digital signal processor, which provides a signal processing algorithm by a corresponding programming via the control unit 22, in order to perform the computationally intensive signal evaluation already on the level of the receiver controller 134.

In order to for example compensate for thermal drifts, ageing processes, contaminants on the transmitting/receiving path of the ultrasonic signal 136 and the like effects, the measurement of the grammage or of the layer thickness of the material sheet 100 is interrupted in presettable or predefined time intervals for calibration. To this, the transmitting and receiving head 112, 114 (group 108) moves laterally out of the measuring section or path (width of the material sheet 100) into the parking position 118. If the correct position of the transmitting and receiving head 112, 114 is detected by means of the position sensor 128, the control unit 22 controls the motor 124 such that the calibration sample 122 clamped in the clamping ring 120 is rotated between transmitting head and receiving head. The center of the transmitting/receiving surface of the transmitting/receiving head 112, 114 is offset radially to the center of the calibration sample 122 such that the center of the transmitting/receiving head is moved relatively to the calibration sample on a circular orbit.

During rotation of the calibration sample 122, ultrasonic transmit pulses are continuously transmitted by the transmitting head 112 and detected by the receiving head 114. Thereby, the transmission values from the calibration sample 122 are measured at different positions distributed over the surface of the calibrations sample. The measured values are recorded by means of the control unit 22. After one-time or multiple-time rotation of the calibration sample 122, the control unit 22 forms an average from the measured transmission values and uses it to calibrate the calibration curve for the grammage determination or layer thickness determination by the traversing measuring group 108.

FIG. 8 shows exemplarily and schematically with the curve t a calibration curve for the intensity I of the transmission of the ultrasonic signal 136 (cf. signal 14 in FIG. 2) depending on the thickness d (the same also applies to the grammage) of the material sheet 100. If the averaging of the previously described determined transmission measurement results in a deviating calibration value for the layer thickness d or the grammage, thus, the calibration curve is correspondingly upwardly or downwardly corrected.

Thereby, a newly calibrated calibration curve is available after the calibration and the layer thickness measurement by means of the measuring group 108 transversely to the material sheet 100 can be continued with the new calibration curve such that the grammage or layer thickness determinations can be performed with higher reliability.

As illustrated in the configuration of the measuring unit 2b in FIG. 10, the measuring unit includes both the traversing measuring group 108 (i.e. reciprocating across the material sheet 100) as well as the stationary array with the (here twelve) transmitting/receiving pairs 10/12. The measuring group 108 is absolutely calibrated in the calibration station 116 by means of the sample 122. The calibrated measuring group 108 is then used to calibrate the transmitting/receiving pairs 10/12 as follows. The cooperation of material sheet 100 moved in longitudinal direction x and measuring group 108 reciprocating in transverse direction y results in the zigzag-shaped sampling path t illustrated dotted in FIG. 10.

Along the sampling path t, the measuring group 108 detects measurement values of the layer thickness and/or the grammage with the repetition rate of the pulsed measurement (cf. FIG. 6). Therein, the path t also sweeps the center of the measurement region of the transmitting/receiving pairs 10/12 extending in the longitudinal direction x, which is exemplarily illustrated dot-dashed with lines for the pair 10/12 in line I, column d (in the following referred to as "(I, d) pair 10/12"). For this example, the five measurement points m1 to m5 are the crossing points of the crossing measuring lines or paths s and t. For calibration of this (I, d) pair 10/12, for example, the average of the five measurement points m1-m5 for the thickness and/or the grammage each for the measurement by means of the measuring group 108 and the measurement by means of the (I, d) pair 10/12 is formed, and if they deviate from each other, the calibration value for the (I, d) pair 10/12 is newly set such that the averaged values for the measurement points m1 to m5 between measuring group 108 and (I, d) pair 10/12 coincide. At least, the new calibration value is used in the following measurements for the (I, d) pair 10/12 until it again has been calibrated against the measuring group 108. In this manner, the other transmitting/receiving pairs 10/12 are calibrated with the corresponding measurement values on the crossing points of the sampling path t and the associated measuring lines of the transmitting/receiving pair 10/12 extending in x direction. This represents a relative calibration of the transmitting/receiving pairs 10/12 against the measuring group 108.

The feedback of the measurement value of the layer thickness or the grammage of the material sheet from the transmitting/receiving pairs 10/12 via the control unit 22 and the control unit 101 for adjusting the actuators 106 on the extrusion die 102 allows a substantially faster control as if for example only the reversing measuring group 108 would be used for measuring and controlling. Moreover, in the measurement at the material sheet 100 and when using only the reversing measuring group 108 it is not possible to identify whether a thickness variation in the longitudinal profile (direction x) or transverse profile (direction y) of the sheet 100 has occurred. A thickness variation in the longitudinal profile for example occurs if the sheet transport proceeds unstably or the foil material exits the die 102 non-uniformly (e.g. on the whole width) due to pressure variations in the extruder. A thickness variation in the transverse profile for example occurs if an individual actuator 106 operates non-uniformly or differently or the die 102 is locally occluded at one or more of the actuators.

In an embodiment, in the measuring unit 2b too, the transmitting heads 112 and opposing the receiving heads 114 can be arranged on a transmitting block 6 and receiving block 8 y-displaceable synchronously with each other as in the measuring unit 2a.

Figure 12:
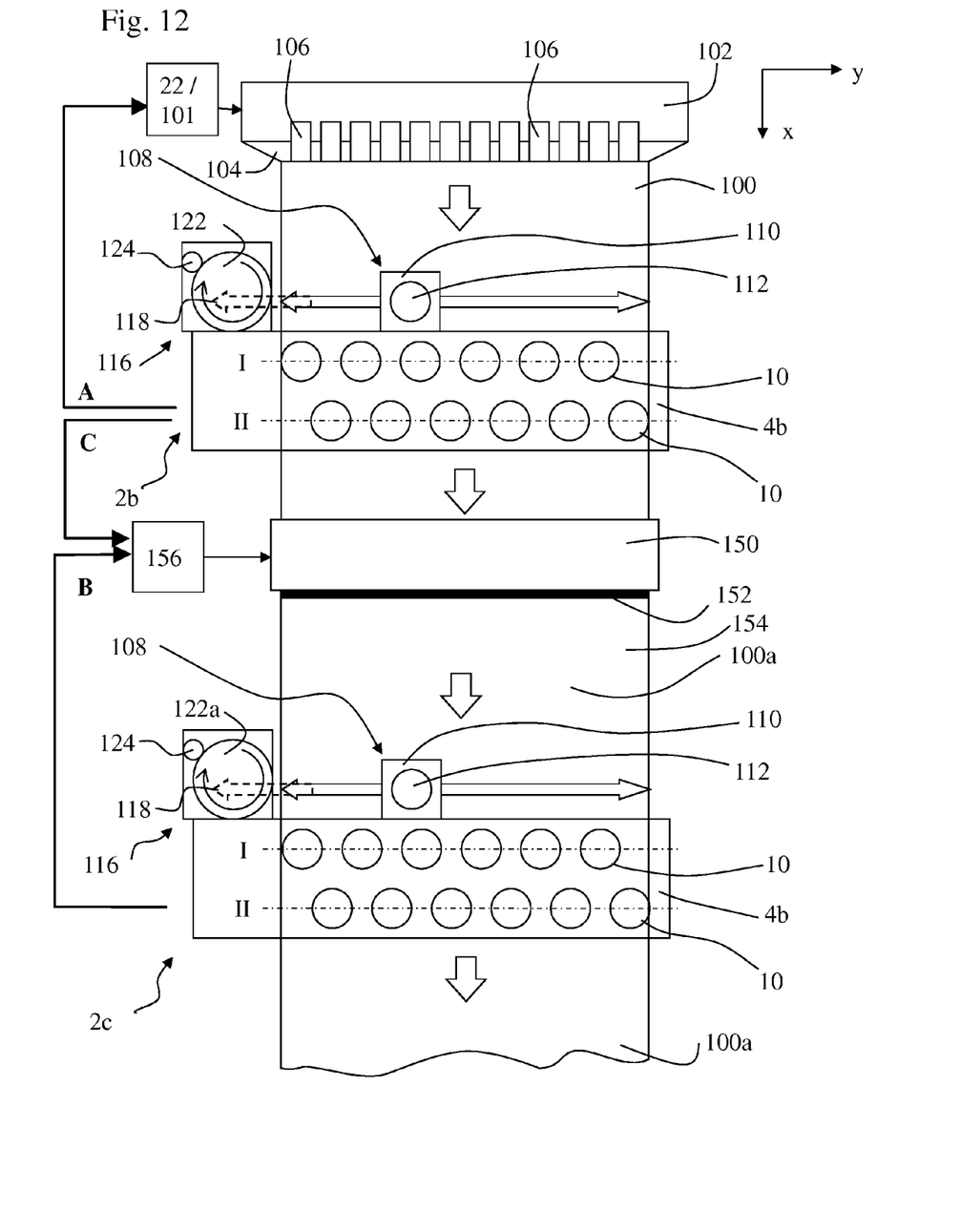
FIG. 12 is a schematic plan view of an arrangement comprising a material sheet production station and coating station each having assigned a measuring unit according to another embodiment.

FIG. 12 shows another embodiment of the invention in which two thickness measurement units 2b and 2c are arranged in series to measure the thickness and/or grammage of the previously produced material sheet 100 by unit 2b and subsequently to measure the thickness and/or grammage of a coating 154 or film on the material sheet 100.

The upper arrangement (as to be seen in FIG. 12) comprising the extrusion die 102 for forming the material sheet 100 and the measuring unit 2b for measuring the thickness/grammage of the material sheet is identical to the arrangement shown in and described with respect to FIG. 10. Thus for detail description reference is made to the above.

The material sheet 100 having passed the measuring unit 2b enters into a calender 150 and passes there between rollers (not shown) where an initially fluid material is applied as a thin coating 154 onto one of the surfaces of the material sheet 100. The material sheet exiting the calender 150 has the coating 154 thereon and is thus denoted as coated material sheet 100a.

An arrangement of two rollers with a variable gap there between is indicated by 152. By adjusting the gap between the rollers the thickness of the coating applied to the surface of the material sheet can be adjusted. Relating to the working principle of the calender 150 reference is made to http://en.wikipedia.org/wiki/Calender which is included herein by reference. The gap between the rollers is adjusted by actuators (not shown) which are controlled by a control unit 156 of the calender.

The measuring unit 2c for measuring the thickness/grammage of the coating 152 on the material sheet 100 is configured and designed essentially exactly as the measuring unit 2b for measuring the thickness/grammage of the material sheet 100. This also relates to the standby and calibration station 116. The main difference is that in the calibration station 116 the calibration sample 122, which is provided as a reference for calibrating the ultrasonic transmitter/receiver pairs 10/12 with respect to the continuously produced material sheet 100, is replaced by a calibration sample 122a. The calibration sample 122a is a reference for the coated material sheet 100a and preferably is a reference sample of the material sheet coated with a reference coating of the coating 154, more preferably a sample having an accurately known average thickness and/or grammage for both, the reference material sheet and the reference coating. The calibration of the sensor pairs 10/12 is made as described above for measuring unit 2b.

Currently measured values for the thickness/grammage are provided from the measuring unit 2c via signal lines B to the control unit 156 of the calender 150, wherein the control unit 156 determines deviations between the set value for the thickness/grammage of the coating 154. In case of unacceptable deviations, the control unit 156 sends control signals to the actuators of the calender 150 which adjust the gap width between the variable gap rollers for adjusting the coating thickness towards the intended thickness/grammage value (set value).

In a first embodiment for measuring and determining thickness/grammage of the coating 154 for adjusting the coating thickness/grammage to the intended value, it can be assumed that the thickness/grammage of the material sheet 100 entering into the calender 150 is constant and sufficiently close to the intended thickness/grammage value (e.g. meeting the supplier's specification). Then determining the thickness/grammage of the coating and adjusting the thickness/grammage of the coating 154 on the material sheet 100 is made in form of a stand-alone (closed control-loop) process with the steps or elements:

supplying the material sheet 100 of known thickness/grammage to the calender 150, coating the material sheet 100 with the coating 154 in the calender, determining the thickness/grammage of the coating 154 or of the coated material 100a using the measuring unit 2c, calculating the thickness/grammage of the coating 154 in the control unit 156, if applicable after subtracting the known thickness/grammage of the material sheet, determining a deviation between the set value and calculated current value for the thickness/grammage of the coating, and adjusting the coating thickness/grammage, if required.

In a second embodiment for measuring and determining thickness/grammage of the coating 154 for adjusting the coating thickness/grammage to the intended value, the thickness/grammage of the material sheet 100 is not assumed to be known (and hence constant), but current values for the thickness/grammage of the material sheet 100 is supplied from the measuring unit 2b via signal lines C to the control unit 156 of the calender 150. The same process as above is implemented with the difference that the thickness/grammage as determined by the measuring unit 2b is subtracted or considered in the calculation of the thickness/grammage for the coating 154. By using the known distance between the detection locations of the two measuring units 2b and 2c and the known conveyance speed of the material sheet 100, the time delay is known between the time when the current thickness/grammage value was determined by measuring unit 2b and the time when this position with the detected value for the thickness/grammage of the material sheet 100 is passing through the measuring unit 2c. Signal line A in FIG. 12 corresponds to the signal line between 22 and 101 shown in FIG. 11.

In a further embodiment (not shown) an arrangement comprising the calender 150 and the measuring unit 2c is provided. I.e. the arrangement shown in FIG. 10 is omitted in the arrangement shown in FIG. 12. For example the pre-manufactures material sheet 100 is not supplied from an extrusion die 102, but instead from a material sheet magazine having a material sheet conveyor or transporting device for transporting the material sheet 100 from the magazine to the calender 150 and out from the calender 150 (e.g. into a magazine for the coated material sheet 100a). The material magazine(s) may be a foil or sheet roller or bobbin.

In further embodiments the coating calender 150 may be replaced by any other coating device applying a thin film coating onto the material sheet 100. For example screen printing device, a printing device, a sol-gel coating device, a varnishing device, a dip-coating device, a laminating device, a CVD or PVD device, a doctor knife or blade coating device, or a powder or spray coating device.

In further embodiments the extrusion die 102 may be any other material sheet (e.g. foil or thin plate) producing device, for example a blow-molding device, a calender, a coextruding die, a foil casting machine, or a foil rolling machine.

Preferably any of the exemplary coating devices and/or material sheet producing devices has an adjustable gap and/or an adjustable expelling nozzle such that the coating thickness or material sheet thickness can be adjusted along the transverse extension (i.e. the y-direction shown in the figures). An adjustment can be made for example using one, two, three, four or more actuators (e.g. as mentioned above) that are distributed along the transverse extension.

For example a first actuator is arranged at the right side of a nozzle or roller and a second actuator is arranged at the left side of the nozzle or actuator. By adjusting the gap or rollers spacing with the first actuator, the thickness of the coating or material sheet can be adjusted in a wedge-like manner from the right side, wherein the thickness-adjustment by the first actuator is the highest on the right side and linearly decreases towards the left side so that no thickness change is caused at the left side, when the second actuator is not actuated. Vice versa this applies when the second actuator is actuated. In this arrangement, if the thickness is to be uniformly changed along the transverse extension, the first and second actuators are actuated in the same sense by the same amount to cause a homogeneous change of the gap width or roller distance along the whole transverse or y-extension.

It will be understood that various aspects or details of the invention may be changed without departing from the scope of the invention. Furthermore, the foregoing description is for the purpose of illustration only, and not for the purpose of limitation—the invention being defined by the claims.

LIST OF REFERENCE CHARACTERS 2, 2a, 2b, 2c measuring unit
4, 4b portal
6 transmitting block
7 material passage slot
8 receiving block
10, 10a ultrasonic transmitter
12 ultrasonic receiver
14 ultrasonic signal lobe
15 reflection signal
16 transmitting controller
18 transducer
20 signal line
22 main control unit
24 signal sequence
28, 28a receiving controller
29 group controller
30, 30a control line
31 signal switch
32, 32a receive signal line
100 material sheet
100a coated material sheet
101 control unit extruder
102 extrusion die
104 die lip
106 actuator
108 reversing measuring group
110 carriage console
112 transmitting head
114 receiving head
116 standby and calibration station
118 parking/calibration position
120 clamping ring
122 calibration sample
122a calibration sample for coating on material sheet
124 drive motor
126 pinion
128 position sensor
132 transmitter controller
134 receiver controller
136 transmission beam
150 coating calender
152 variable gap rollers
154 coating
156 control unit for calender
A, B, C control signal lines
I intensity
P intensity profile
D diameter transmitting surface
O overlap in projection
T transmission curve
R reflection curve
G time window of the measurement
U dead interval
d material thickness
m1 ... m5 calibration measurement points
s longitudinal measuring path
t traversing measuring path
x longitudinal direction of material sheet
y transverse direction of material sheet
z surface normal to material sheet
α a column angle of the array
a, b, c, d, e array columns
I, II, III array lines

The invention claimed is:

1. A system comprising:
a thin-material-sheet-producing or coating apparatus configured to produce a thin material sheet or configured to produce a coated thin material sheet, the apparatus including
an elongated nozzle or gap characterized by an outlet gap width and configured to expel the thin material sheet, or including a gap member adapted to apply a coating layer onto a surface of the thin material sheet,
an actuator adapted to adjust a thickness of the thin material sheet by adjusting the outlet gap width of the elongated nozzle or gap, or adapted to adjust a thickness of the coating layer by adjusting a gap width of the gap member, and
a control unit adapted to control the actuator for expelling the thin material sheet with a predetermined thickness or adapted for coating the material sheet with a predetermined coating layer thickness; and
an ultrasonic device for determining a layer thickness and/or a grammage of the thin material sheet or of the coating layer on the thin material sheet, the ultrasonic device including a plurality of ultrasonic transmitters,
a number of ultrasonic receivers, wherein the number of the ultrasonic receivers corresponds to the number of, or corresponds to twice the number of, the plurality of ultrasonic transmitters,
one receiver electronics respectively for each of the number of ultrasonic receivers, or a group receiver electronics respectively for a predetermined plurality of ultrasonic receivers of the number of ultrasonic receivers;
wherein the control unit is further adapted to receive a measurement value for the layer thickness and/or the grammage from the ultrasonic device, and
wherein the control unit is configured to control, in dependency on the measurement value, the actuator to either adjust the outlet gap width of the elongated nozzle or gap, or to control the gap width of the gap member.

2. The system of claim 1, wherein the ultrasonic transmitters of the ultrasonic device are distributed on a first supporting device and wherein the ultrasonic device is arranged such that when the thin material sheet is to be measured while moving in a longitudinal direction, the ultrasonic device is parallel to the moving thin material sheet and the first supporting device extends perpendicularly or substantially perpendicularly to the longitudinal direction.

3. The system of claim 1, wherein the ultrasonic transmitters are spatially distributed such that, when the thin material sheet is to be measured while moving in a longitudinal direction, the ultrasonic transmitters span a distance in a transverse direction and span a distance over a predetermined depth in the longitudinal direction, wherein the transverse and longitudinal directions are substantially perpendicular and define a plane parallel to the thin material sheet.

4. The system of claim 3, wherein the ultrasonic transmitters are spatially distributed such that the ultrasonic transmitters are arranged in multiple lines, each line extending in the transverse direction, wherein the ultrasonic transmitters of each line are evenly offset to each other in the transverse direction, and wherein the lines are evenly spaced apart in the longitudinal direction.

5. The system of claim 4, wherein the ultrasonic transmitters are configured in a two-dimensional lattice, each ultrasonic transmitter characterized by its transverse and longitudinal coordinates in the lattice.

6. The system of claim 5, wherein the transverse coordinate for each ultrasonic transmitter is different, and the transverse coordinates of the ultrasonic transmitters are evenly spaced.

7. The system of claim 1, wherein the ultrasonic transmitters are oriented such that, when a thin material sheet is to be measured, the ultrasonic transmitters emit radiation in a radiation direction oriented perpendicularly or approximately perpendicularly to a surface of the thin material sheet, and wherein the respective ultrasonic receivers associated with the ultrasonic transmitters are arranged such that each ultrasonic receiver is positioned to receive the ultrasonic radiation from its associated ultrasonic transmitter through a thickness of the thin material sheet.

8. The system of claim 2, wherein the ultrasonic receivers are arranged on a second supporting device paired to an arrangement of the ultrasonic transmitters, wherein the second supporting device is arranged at a side of the material sheet opposing the first supporting device.

9. The system of claim 1, wherein each of the receiver electronics or group receiver electronics comprises an amplifier in which the amplification is adjustable, in multiple amplification stages.

10. The system of claim 9, wherein each of the receiver electronics comprises a signal processor for evaluating the signal received from the associated ultrasonic receiver, wherein the signal processor is implemented in a microcontroller.

11. The system of claim 1, further comprising a main control unit for generating a transmit signal, wherein the main control unit is connected to each of the ultrasonic transmitters and supplies the transmit signal to each of the ultrasonic transmitters, wherein the transmit signal is supplied to all of the ultrasonic transmitters at the same time or with a slight temporal offset.

12. The system of claim 1, further comprising a measuring group or sensor unit with a transmitting head and a receiving head, wherein the measuring group or sensor unit is movable in a transverse direction when the thin material sheet is being measured while moving in a longitudinal direction, wherein the transverse and longitudinal directions are substantially perpendicular and define a plane parallel to the thin material sheet.

13. The system of claim 12, wherein a calibration station is assigned to the measuring group or sensor unit, at which the measuring group or sensor unit can be calibrated by means of a calibration sample.

14. The system of claim 12, wherein each of the ultrasonic transmitter and receiver pairs can be calibrated by a control unit of the ultrasonic device by evaluation of measurement results of the measuring group or sensor unit measured at the thin material sheet and of measurement results of the ultrasonic transmitter and receiver pairs measured at the thin material sheet.

15. The system of claim 1, wherein the thin-material-sheet-producing or coating apparatus is a foil extruder having an extrusion die, and
wherein the actuator is configured to adjusting the foil thickness by adjusting the outlet gap width.

16. The system of claim 15, wherein a plurality of actuators is arranged at the extrusion die and an ultrasonic transmitter and receiver pair, or each one group of ultrasonic transmitter and receiver pairs, is associated with each actuator, or a group of actuators is associated with each one ultrasonic transmitter and receiver pair, wherein the control unit adjusts or alters an actuator or a group of actuators depending on the measurement signal, or the measurement signals, from the associated ultrasonic transmitter and receiver pair or the group of the ultrasonic transmitter and receiver pairs.

17. The system of claim 1, wherein the thin-material-sheet-producing or coating apparatus is a calender adapted
to coat the thin material sheet with a coating film, or
to produce the thin material sheet.

18. The system of claim 17, wherein the calender has at least one pair of cooperating rollers having an adjustable gap therebetween, wherein the actuator is adapted to set a predefined gap width under the control of the control unit.

19. The system of claim 1, wherein the thin-material-sheet-producing or coating apparatus is a screen printing device, a doctor knife or doctor blade coating device, a flexo or pad coating device, a printing device, a sol-gel coating device, a varnishing device, a dip-coating device, a laminating device, a CVD or PVD device, a powder coating device, or a spray coating device.

20. The system of claim 1, further comprising:
a second system comprising a second thin-material-sheet-coating apparatus and a second ultrasonic device, the second system arranged to receive the thin material sheet or coated thin material sheet from the prior ultrasonic device;
wherein the second system is adapted to coat the thin material sheet or coated material sheet with a coating layer of a predetermined thickness.

21. A method of coating a thin material sheet with a coating of a predetermined thickness using the system of claim 1, the method comprising:
supplying the thin material sheet to the thin-material-sheet-producing or coating apparatus of the system;
coating the thin material sheet with a coating layer in the thin-material-sheet-producing or coating apparatus;
determining a thickness/grammage of the coating layer or of the coated thin material sheet using the ultrasonic device of the system;
determining a difference between the predetermined thickness and the determined thickness/grammage of the coating layer; and
adjusting the thickness/grammage of the coating layer applied by the thin-material-sheet-producing or coating apparatus in dependence upon the difference.

22. The method of claim 21, wherein the step of determining the thickness/grammage of the coating layer includes subtracting a thickness/grammage of the thin material sheet from a measured value determined by the ultrasonic device of the system.

23. The method of claim 22, further comprising, before coating the thin material sheet with the coating layer, determining the thickness/grammage of the thin material sheet using the ultrasonic device of the system.

* * * * *